United States Patent [19]

Hayes et al.

[11] Patent Number: 5,114,945
[45] Date of Patent: May 19, 1992

[54] SPIROPIPERIDINE DERIVATIVES

[75] Inventors: Norman F. Hayes, Hitchin; David I. C. Scopes, Furneux Pelham; Andrew B. McElroy, Watton-at-Stone; Ann G. Hayes, Potters Bar; Clive A. Meerholz, Buntingford, all of United Kingdom

[73] Assignee: Glaxo Group Limited, London, England

[21] Appl. No.: 315,261

[22] Filed: Feb. 23, 1989

[30] Foreign Application Priority Data

Feb. 23, 1988 [GB] United Kingdom ............... 8804014

[51] Int. Cl.⁵ ............... A01N 43/42; A61K 31/44; C07D 491/113; C07D 495/10; C07D 513/10
[52] U.S. Cl. .............................. 514/278; 546/19
[58] Field of Search .......................... 546/19; 514/278

[56] References Cited

U.S. PATENT DOCUMENTS

| | | |
|---|---|---|
| 2,684,965 | 7/1954 | Weston et al. |
| 4,304,911 | 12/1981 | Zenitz |
| 4,579,863 | 4/1986 | Horwell et al. |
| 4,629,739 | 12/1986 | Davey et al. |

FOREIGN PATENT DOCUMENTS

| | | |
|---|---|---|
| 86/66824 | 6/1987 | Australia |
| 0931569 | 8/1973 | Canada |
| 176309 | 4/1986 | European Pat. Off. |
| 233793 | 8/1987 | European Pat. Off. |
| 260041 | 3/1988 | European Pat. Off. |
| 275696 | 7/1988 | European Pat. Off. |
| 0291238 | 11/1988 | European Pat. Off. |
| 0032542 | 8/1974 | Japan |

Primary Examiner—Robert A. Wax
Assistant Examiner—Fred Tsung
Attorney, Agent, or Firm—Bacon & Thomas

[57] ABSTRACT

Compounds are disclosed of formula (I)

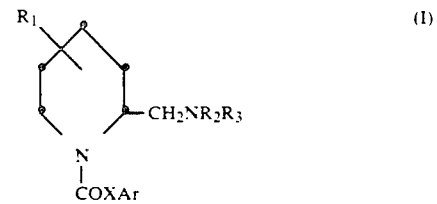

wherein
$R_1$ represents hydroxy, $C_{1-6}$ alkyl, $C_{1-6}$ hydroxyalkyl, $C_{1-6}$ carboxyalkyl, phenyl, oxo, amino, carboxy, amido, $-NR_4COR_5$ (where $R_4$ and $R_5$ both represent $C_{1-6}$ alkyl), optionally substituted methylidene or, together with the carbon atom to which it is attached, $R_1$ forms a 5 or 6-membered ring containing one or more heteroatoms;

$R_2$ and $R_3$ are the same or different and are $C_{1-6}$ alkyl or $C_{3-6}$ alkenyl; or $-NR_2R_3$ forms a 5-membered (optionally containing an oxygen atom adjacent to the nitrogen) or a 6-membered ring, which ring optionally contains one unit of unsaturation and which is unsubstituted or substituted by hydroxy, oxo, optionally substituted methylidene, $-COR_6$ (where $R_6$ represents $C_{1-6}$ alkyl, OR, or $-NHR$, and R represents hydrogen, $C_{1-6}$ alkyl, aryl, ar($C_{1-6}$) alkyl) or $=NOR_8$ (where $R_8$ represents $C_{1-6}$ alkyl);

X represents a direct bond, $-CH_2-$ or $-CH_2O-$;
Ar represents a substituted phenyl moiety;
and physiologically acceptable salts thereof.

The compounds are indicated as useful for the treatment of pain and cerebral ischemia.

Proccesses and intermediates for their preparation and pharmaceutical compositions containing them are also disclosed.

10 Claims, No Drawings

SPIROPIPERIDINE DERIVATIVES

This invention relates to piperidine derivatives, to processes for their preparation, to pharmaceutical compositions containing them and to their medical use. In particular, the invention relates to compounds which act as agonists at kappa opioid receptors.

Compounds which are kappa opioid receptor agonists have been indicated in the art for the treatment of a number of conditions and have been described, for example, as analgesics, as diuretics and in the treatment of cerebral ischaemia. Opioid analgesia is generally though to be mediated by either mu or kappa receptors in the brain (see, for example, Tyers, M. B., Br. J. Pharmacol. (1980), 69, 503–512). Most existing clinically used opioid analgesics such as morphine and codeine act as mu-receptor agonists. However, these compounds have undesirable and potentially dangerous dependence forming side effects. There is thus a need for a strong analgesic with low dependence liability and a compound which is a selective kappa-receptor agonist would fulfil such a role.

Cerebral ischaemia or lack of blood flow in the brain, may result from a number of conditions, including, for example, stroke, head injuries or brain tumour. The resulting lack of oxygen to the brain cells causes neuronal damage and depending on the region of the brain involved, death or permanent disability may occur.

We have now found a novel group of piperidine derivatives which are selective kappa opioid receptor agonists. These compounds are therefore of interest in the treatment of conditions where the underlying aetiology indicates that treatment with a kappa opioid receptor agonist would be beneficial.

Thus, the present invention provides compounds of formula (I):

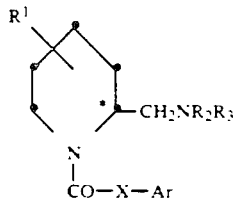

wherein $R_1$ represents hydroxy, $C_{1-6}$ alkyl, $C_{1-6}$ hydroxyalkyl, $C_{1-6}$ carboxyalkyl, phenyl, oxo, amino, carboxy, amido, —$NR_4COR_5$ (where $R_4$ and $R_5$ both represent $C_{1-6}$ alkyl), optionally substituted methylidene or, together with the carbon atom to which it is attached, $R_1$ forms a 5 or 6-membered ring containing one or more heteroatoms;

$R_2$ and $R_3$ are the same or different and are $C_{1-6}$ alkyl or $C_{3-6}$ alkenyl; or —$NR_2R_3$ forms a 5-membered (optionally containing an oxygen atom adjacent to the nitrogen) or a 6-membered ring, which ring optionally contains one unit of unsaturation and which is unsubstituted or substituted by hydroxy, oxo, optionally substituted methylidene, —$COR_6$ (where $R_6$ represents $C_{1-6}$ alkyl, $OR_7$ or —$NHR_7$, and $R_7$ represents hydrogen, $C_{1-6}$ alkyl, aryl, ar($C_{1-6}$)alkyl) or =$NOR_8$ (where $R_8$ represents $C_{1-6}$ alkyl);

X represents a direct bond, —$CH_2$— or —$CH_2O$—;

Ar represents a substituted phenyl moiety; and physiologically acceptable salts thereof.

It is not intended to include within the scope of the present invention compounds in which any position on the piperidine ring contains more than one distinct substituent. It will be appreciated by one skilled in the art that certain substituents attached to the carbon atom adjacent to the nitrogen atom in the piperidine ring will be readily susceptible to hydrolysis. It is also intended to exclude such compounds from the present invention.

As used herein, a $C_{1-6}$ alkyl group or the alkyl moiety of an ar($C_{1-6}$)alkyl, $C_{1-6}$ hydroxyalkyl or $C_{1-6}$ carboxyalkyl group may be straight or branched chain and is conveniently $C_{1-4}$ alkyl for example methyl or ethyl. A $C_{1-6}$ hydroxyalkyl group may be, for example, a hydroxymethyl group. A $C_{1-6}$ carboxyalkyl group may be, for example, methoxycarbonylmethyl. An aryl group or the aryl moiety of an ar($C_{1-6}$)alkyl group is preferably phenyl. Where $R_1$ represents a group —$NR_4COR_5$, $R_4$ and $R_5$ each preferably independently represents a methyl group.

It will be appreciated that where $R_1$ together with the carbon atom to which it is attached forms a 5 or 6-membered ring, this will form a spiro system with the piperidine ring. The ring formed by $R_1$ may conveniently contain one or more oxygen, sulphur or nitrogen atoms and may be, for example, 1,3-dithiolane, 1,3-dioxalane or thiazolidine.

An alkenyl group may be a straight or branched chain group. Where $R_2$ and/or $R_3$ in the compounds of formula (I) represents an alkenyl group, it will be appreciated that a double bond will not be attached to the carbon atom adjacent to the nitrogen.

The term 'optionally substituted methylidene' is intended to cover methylidene substituted by any substituent conventional in the art. In the compounds of formula (I), the methylidene group may conveniently be substituted to form a conjugated system. Suitable substituents which form a conjugated system with the methylidene double bond include, for example, nitrile, phenyl, carboxyl and amido. Alternatively the methylidene group may conveniently be substituted by, for example, by a $C_{1-6}$ alkyl group, an ar($C_{1-6}$)alkyl group such as phenethyl, a $C_{1-6}$ hydroxyalkyl group such as hydroxymethyl, a $C_{1-6}$ carboxyalkyl group such as methoxycarbonylethyl or a $C_{1-6}$ amidoalkyl group such as aminocarbonylethyl.

Where —$NR_2R_3$ forms a substituted or unsubstituted 5 or 6-membered ring optionally containing one unit of unsaturation this may be, for example, a substituted or unsubstituted pyrrolidine, isoxazolidine or tetrahydropyridine ring. It will be appreciated that where the ring formed by —$NR_2R_3$ contains a unit of unsaturation, this will not be attached to a carbon atom adjacent to the nitrogen atom.

The term 'a substituted phenyl moiety' is intended to cover a phenyl moiety substituted by one or more conventional substituents in the art, which substituents may form a second ring optionally containing one or more units of unsaturation. In the compounds of formula (I), Ar conveniently represents a phenyl moiety which is substituted by one or more $C_{1-6}$ alkyl groups or electron-withdrawing substituents, or in which two adjacent substituents form a second ring. Suitable electron-withdrawing substituents include, for example, halogen (for example, fluorine, chlorine or bromine), —$CF_3$ or —$NO_2$. Where two substituents on the phenyl ring form a second ring, Ar may suitably represent naphthyl, for example 1-naphthyl or 2-naphthyl. Ar preferably represents phenyl substituted, preferably at the meta and/or para positions on the phenyl ring, by one or more halogen atoms, for example chlorine and is typically a 3,4-dichlorophenyl moiety.

Conveniently $R_1$ may be, for example, a group —$CH_3$, —$CH_2OH$, —$CO_2CH_3$, —$N(CH_3)COCH_3$ and when attached at the 3,4 or 5 positions of the piperidine ring $R_1$ may additionally represent, for example, —OH, —$NH_2$, =O, =$CH_2$, phenyl, phenylpropylidene, =$CHCO_2CH_3$, 1,3-dioxalane, 1,3-dithiolane or thiazolidine.

$R_2$ and $R_3$ may each independently represent a $C_{1-6}$ alkyl group such as methyl, or —$NR_2R_3$ may suitably represent a pyrrolidine or tetrahydropyridine ring which may be optionally substituted, for example, by —$CO_2CH_3$, preferably by —OH, =$CH_2$, =$NOCH_3$, —$CONH_2$ or more preferably by =O, =CHCN or =$CHCO_2CH_3$. Where the ring formed by —$NR_2R_3$ is substituted by substituted methylidene the substituent is preferably in the Z configuration.

$R_1$ preferably represents a $C_{1-6}$ alkyl group (such as methyl), an oxo group or together with the carbon atoms to which it is attached $R_1$ forms a 5- or 6-membered ring containing one or more heteroatoms such as a 1,3-dithiolane, 1,3-dioxalane or thiazolidine ring.

In a particularly preferred group of compounds of formula (I), $R_1$ represents a 1,3-dithiolane, 1,3-dioxalane or thiazolidine ring.

In the compounds of formula (I), $R_1$ is preferably attached to the 3,4 or 6-position of the piperidine ring.

—$NR_2R_3$ may represent a substituted tetrahydropyridine or pyrrolidine ring but —$NR_2R_3$ preferably represents an unsubstituted tetrahydropyridine or more preferably an unsubstituted pyrrolidine ring. Where —$NR_2R_3$ represents a substituted ring, the substituent is preferably attached to the carbon atom $\beta$ to the nitrogen atom.

X preferably represents —$CH_2$—.

A preferred class of compounds falling within the scope of formula (I) is that in which $R_1$ represents —$CH_3$, =O, 1,3-dioxalane, 1,3-dithiolane or thiazolidine; —$NR_2R_3$ forms an unsubstituted pyrrolidine or tetrahydropyridine ring and physiologically acceptable salts.

One group of preferred compounds of formula (I) falling within this class is that in which $R_1$ represents —$CH_3$ and the substituent $R_1$ is attached at the 3- or 6-position of the piperidine ring.

Another group of preferred compounds of formula (I) falling within this class is that in which $R_1$ represents =O, 1,3-dioxalane, 1,3-dithiolane or thiazolidine and the substituent $R_1$ is at the 4-position of the piperidine ring.

In this class of compounds, X preferably represents —$CH_2$— and Ar preferably represents halosubstituted phenyl. Particularly preferred compounds falling with this class are those in which Ar represents chlorosubstituted phenyl and in particular 3,4-dichlorophenyl.

Preferred compounds of the invention include:
1-[(3,4-Dichlorophenyl)acetyl]-2-(1-pyrrolidinylmethyl)-4-piperidinone;
8-[(3,4-Dichlorophenyl)acetyl]-7-[(1,2,3,6-tetrahydropyridin-1-yl)methyl]-1,4-dioxa-8-azaspiro[4.5]-decane
1-[(3,4-Dichlorophenyl)acetyl]-3-methyl-2-(1-pyrrolidinylmethyl)piperidine;
cis-1-[(3,4-Dichlorophenyl)acetyl]-2-methyl-6-(1-pyrrolidinylmethyl)piperidine;
and physiologically acceptable salts thereof.

Particularly preferred compounds of the invention include:
8-[(3,4-Dichlorophenyl)acetyl]-7-(1-pyrrolidinylmethyl)-1,4-dioxa-8-aza[4.5]spirodecane;
8-[(3,4-Dichlorophenyl)acetyl]-7-(1-pyrrolidinylmethyl)-1-thia-4,8-diazaspiro[4.5]decane;
8-[(3,4-Dichlorophenyl)acetyl]-7-(1-pyrrolidinylmethyl)-1,4-dithia-8-azaspiro[4.5]decane;
and the physiologically acceptable salts thereof.

Compounds of formula (I) contain at least one chiral centre (shown in formula (I) by *) and may exist in more than one stereoisomeric form. The invention includes within its scope all enantiomers, diastereomers and mixtures thereof. The preferred stereoisomeric form of the compounds of formula (I) are those represented by the formula (Ia):

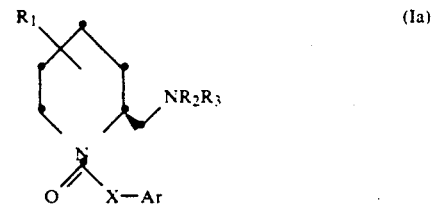

wherein $R_1$, $R_2$, $R_3$, X and Ar are as defined for formula (I). The invention also embraces all geometric isomers of compounds of formula (I).

Suitable physiologically acceptable salts are those conventionally known in the art. Examples of physiologically acceptable salts include acid addition salts formed with inorganic acids, such as hydrochlorides, hydrobromides, phosphates and sulphates, and with organic acids, for example tartrates, maleates, fumarates, succinates and sulphonates. Other salts which are not pharmaceutically acceptable may be useful in the preparation of compounds of formula (I) and these form a further part of the invention. Compounds of the invention may readily be isolated in association with solvent molecules by crystallisation from or evaporation of an appropriate solvent. It is intended to include such solvates within the scope of the present invention.

Compounds falling within formula (I) have been shown to have analgesic activity using standard laboratory animal tests such as the mouse acetylcholine writhing test (M. B. Tyers, *Brit. J. Pharmacol*, 1980, 69, 503–512) or the rat paw pressure test. Furthermore, their selective kappa receptor activity has been demonstrated in vitro in the field stimulated rabbit vas deferens preparation using the procedure described by A. G. Hayes and A Kelly, *Eur. J. Pharmacol* 110, 317–322 (1985). Compounds of the invention and their physiologically acceptable salts and solvates thus possess analgesic activity with the potential for low dependence liability and are therefore useful in the relief of pain.

Compounds of the invention are also of value in protecting against neuronal damage resulting from cerebral ischaemia which may be demonstrated for example in standard laboratory bilateral carotid occlusion models. Thus, compounds of the invention and their physiologically acceptable salts are also useful in treating or relieving the effects of cerebral ischaemia.

Accordingly, the invention also provides a compound of formula (I) or a physiologically acceptable salt thereof for use in medicine, in particular for the treatment of conditions where kappa agonists are indicated, (for example as analgesics and in the treatment of cerebral ischaemia).

In an alternative or further aspect there is provided a method of treatment of a mammal, including man, comprising administration of an effective amount of a compound of formula (I) or a physiologically acceptable salt thereof in particular in the treatment of conditions where the use of a kappa receptor agonist is indicated.

It will be appreciated that compounds of the invention will primarily be of use in the alleviation of established symptoms but prophylaxis is not excluded.

Compounds of the invention may be administered as the raw chemical but the active ingredient is preferably presented as a pharmaceutical formulation. The active ingredient may conveniently be presented in unit dose form.

According to another aspect, the invention provides a pharmaceutical composition comprising at least one compound of formula (I) or a physiologically acceptable salt thereof and formulated for administration by any convenient route conventional in the art. Such compositions are preferably in a form adapted for use in medicine, in particular human medicine and can conveniently be formulated in conventional manner using one or more pharmaceutically acceptable carriers or excipients. Compounds according to the invention may conveniently be formulated for oral or parenteral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example almond oil, oily esters or ethyl alcohol); and preservatives (for example methyl or propyl-p-hydroxybenzoates or sorbic acid).

The compounds of the invention may be formulated for parenteral administration by injection, preferably intravenous or subcutaneous injection, for example by bolus injection or continuous intravenous infusion. Where the compounds are administered by continuous intravenous infusion this is conveniently sequential to a bolus injection. Formulations for injection may be presented in unit dosage form, for example, in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed dose of the compounds of the invention for the relief of pain or the treatment of cerebral ischaemia is 0.01 to 100 mg/kg body weight, preferably 0.01 to 10 mg/kg body weight, most preferably 0.1 to 10 mg/kg body weight per day.

The invention also provides the use of a compound of formula (I) or a physiologically acceptable salt thereof for the manufacture of a medicament for the treatment of conditions where kappa receptor agonists are indicated.

According to another aspect of the invention, compounds of formula (I) and physiologically acceptable salts thereof may be prepared by the general methods outlined below. In the following methods, $R_1$, $R_2$, $R_3$, X and Ar are as defined for formula (I) unless otherwise indicated.

It will be appreciated that in the methods for preparing compounds of formula (I) given below, it may be necessary or desirable to protect one or more sensitive groups in the molecule to prevent undesirable side reactions. Thus, a reaction step involving deprotection of a protected derivative of a compound of the invention may be required subsequent to any of the processes described below. Protection and deprotection may be effected using conventional procedures as described, for example, in 'Protective Groups in Organic Synthesis', T. W. Greene (John Wiley & Sons, 1981).

According to one general process (A), compounds of formula (I) may be prepared by reacting a compound of formula (II)

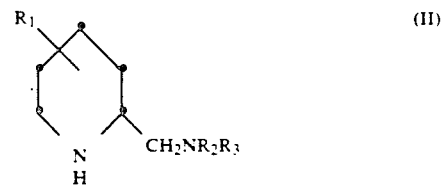

with a reagent serving to introduce the group —COXAr.

Thus, for example, compounds of formula (I) may be prepared by reacting a compound of formula (II) with an acid ArXCO$_2$H or an acylating agent corresponding thereto or a salt thereof.

Suitable acylating agents corresponding to the acid ArXCO$_2$H which may conveniently be used include, for example, acid halides (for example acid chlorides), alkyl esters (for example, methyl or ethyl esters) and mixed anhydrides. Such acylating agents may conveniently be prepared from the acid itself by conventional methods.

The reaction of a compound of formula (II) with an acid ArXCO$_2$H is desirably effected in the presence of a coupling agent such as carbonyl diimidazole, dicyclohexylcarbodiimide or diphenylphosphoryl azide in a suitable reaction medium and conveniently at a temperature of from $-50°$ to $+50°$ C., preferably at room temperature. The reaction may be effected in a suitable reaction medium such as an ether (for example tetrahydrofuran), a haloalkane (for example, dichloromethane), a nitrile (for example acetonitrile), an amide (for example dimethylformamide), or mixtures thereof.

The reaction of a compound of formula (II) with an acylating agent corresponding to the acid $ArXCO_2H$ may conveniently be effected using the reaction conditions described above and optionally in the presence of a base. Suitable bases which may be employed include, for example, organic bases such as pyridine or triethylamine or inorganic bases such as calcium carbonate or sodium bicarbonate.

Compounds of formula (II) may themselves be prepared, for example, from compounds of formula (III)

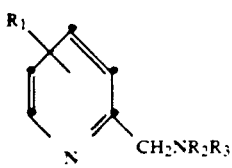

(III)

by reduction using standard conditions followed, if necessary, by conversion of a compound of formula (II) in which $R_1$ has one meaning according to the general definition into a compound of formula (II) in which $R_1$ has another meaning using standard methods of interconversion.

The reduction may conveniently be carried out in the presence of hydrogen and a metal catalyst such as palladium, Raney nickel, platinum, platinum oxide or rhodium which may be supported, for example, on charcoal or alumina.

Compounds of formula (III) are either known compounds or may be prepared from known compounds by conventional methods.

Alternatively, compounds of formula (II) may be prepared from compounds of formula (IV)

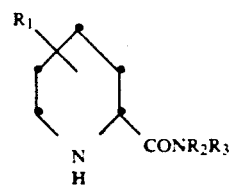

(IV)

by reduction using a suitable reducing agent, for example, a metal hydride such as lithium aluminium hydride in a solvent such as tetrahydrofuran. When suitable, the group $R_1$ may be protected before the reduction to give the corresponding compound of formula (II). Thus, for example, an oxo group may be protected as a spiro cyclic ketal, for example as a 1,3-dioxalane group.

Compounds of formula (IV) may themselves be prepared, for example, from the appropriate carboxylic acid (or an acylating derivative corresponding thereto) by reaction with an amine $HNR_2R_3$ according to the method described above. The starting acid may conveniently be prepared, for example, by reduction of the corresponding tetrahydropyridine or pyridine derivative.

According to another general process (B), compounds of formula (I) may be prepared by reductive amination of a compound of formula (V)

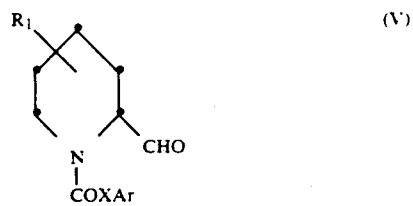

(V)

with an amine $R_2R_3NH$ in the presence of a suitable reducing agent.

The reduction may be effected using an alkali metal or alkaline earth metal borohydride or cyanoborohydride (for example sodium borohydride or cyanoborohydride) in a suitable solvent, for example an alcohol such as methanol and at a suitable temperature, conveniently room temperature. The reaction may optionally be performed in the presence of an acid such as acetic acid.

Alternatively, the reduction may be effected catalytically, for example, using hydrogen in the presence of a metal catalyst such as Raney nickel, platinum, platinum oxide, palladium or rhodium which may be supported, for example, on charcoal. The reaction may conveniently be carried out in a suitable solvent such as an alcohol (for example ethanol), an amide (for example dimethylformamide) an ether (for example tetrahydrofuran) and at a suitable temperature.

Compounds of formula (V) may be prepared, for example, from compounds of formula (VI)

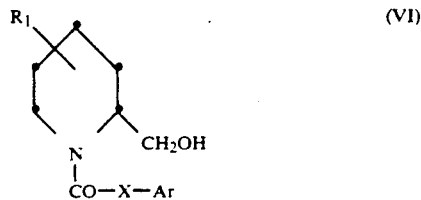

(VI)

by oxidation using conventional methods, for example using an oxidising agent such as chromium trioxide in a suitable solvent, for example pyridine.

Compounds of formula (VI) may themselves be prepared from the corresponding 1-unsubstituted piperidine of formula (VII)

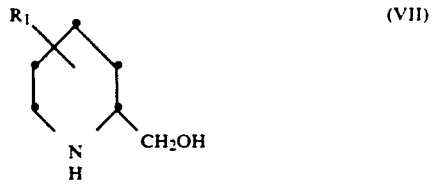

(VII)

by methods analogous to those described for general process (A) above. Compounds of formula (VII) are either known or can be prepared from known compounds by conventional methods.

According to a further general process (C), a compound of formula (I) according to the invention may be converted into another compound of the invention using conventional procedures. It will be appreciated that where a compound of formula (I) contains an identical substituent at more than one position in the molecule, general process (C) covers the conversion of either or both substituents to another substituent falling within the general formula (I).

According to one embodiment of process (C), a compound of formula (I) containing an oxo group at one or more positions in the molecule may be converted into the corresponding optionally substituted methylidene derivative by reaction with an appropriate Wittig reagent, for example a phosphonate (such as trimethylphosphonoacetate) or a phosphorane prepared by reacting an appropriate triarylphosphonium salt (such as methyltriphenylphosphonium bromide) with a base. Suitable bases which may be used include, for example, alkali metal hydrides such as sodium hydride, alkali metal alkoxides such as sodium or potassium t-butoxide or alkali lithiums such as n-butyl lithium. The reaction may conveniently be carried out in a solvent such as an ether, for example tetrahydrofuran, and at a temperature of from $-70°$ to $+50°$.

Compounds of formula (I) in which $R_1$ represents a trans amino group at the 3-position of the piperidine nucleus may be prepared from the appropriate alcohol by azide formation, for example by reaction with an azide (for example diphenylphosphorylazide) in the presence of diethylazodicarboxylate and triphenylphosphine in a solvent such as tetrahydrofuran, and subsequent reduction. Suitable reducing agents which may be used include, for example lithium aluminium hydride or zinc-potassium dihydrogen orthophosphate.

Compounds of formula (I) in which $R_1$ represents a group $-NR_4COR_5$ may be prepared from the corresponding oxo derivative by reductive amination with an appropriate amine $R_4NH_2$ according to the method of general process (B) followed by introduction of the acyl moiety $-COR^5$ by conventional acylation procedures, for example by reaction with an appropriate acid anhydride in the presence of a base such as pyridine, according to the method of general process (A).

Compounds of formula (I) containing a hydroxy group at one or more positions of the molecule can conveniently be prepared by reduction of the corresponding oxo compound using a suitable reducing agent such as an alkali metal borohydride or cyanoborohydride (for example sodium borohydride) or a metal hydride (for example diisobutyl aluminium hydride or lithium aluminium hydride) in a suitable solvent for example, an alcohol (such as ethanol) a hydrocarbon (such as toluene), a halogenated hydrocarbon (such as dichloromethane) or an ether (such as tetrahydrofuran). When the reduction is effected on a compound of formula (I) in which $R_1$ represents a hydroxy group attached at the piperidine 4-position using a sterically bulky reducing agent such as that prepared by treating diisobutyl aluminium hydride with 2,6-di-tert-butyl-4-methylphenol, the cis isomer may conveniently be obtained.

Compounds of formula (I) containing one or more oxo groups may be prepared by oxidation of the corresponding alcohol using a suitable oxidising agent, for example an acid anhydride or acid chloride complex with dimethylsulphoxide (such as oxalylchloridedimethylsulphoxide) in a solvent such as dichloromethane, conveniently at low temperature followed by treatment with a base such as triethylamine. Compounds of formula (I) where $R_1$ represents an oxo group may also be prepared by hydrolysis of the corresponding 1,3-dioxolane derivative using conventional methods, for example by reaction with a ketone such as acetone in the presence of an acid such as dilute sulphuric acid at a suitable temperature up to reflux.

Compounds of formula (I) containing an oxime substituent may conveniently be prepared from the corresponding oxo derivative by conventional oximation procedures, for example by reaction with an appropriate amine $R_8ONH_2$ in a suitable solvent such as pyridine, conveniently at room temperature.

Compounds of formula (I) containing a 1,3-dithiolane or thiazolidine substituent may conveniently be prepared from the corresponding oxo substituent by conventional condensation with an appropriate thiol or dithiol.

An amido substituent at one or more positions in the molecule may be prepared from the corresponding carboxy substituted compound of formula (I) according to the method of general process (A) above.

As well as being employed as the last main step in the reaction sequence, the general methods discussed above may also be used to introduce a desired group at any intermediate stage in the preparation of compounds of formula (I). Thus, for example, the required group at the 2-position of the piperidine nucleus in the compounds of the invention can be introduced before or after acylation to introduce the —COXAr moiety. It will be appreciated that the sequence of reactions will be chosen such that the reaction conditions do not affect groups present in the molecule which are required in the final product.

The general processes described above may yield the product of the general formula (I) as an individual stereoisomer or as a mixture of stereoisomers. Diastereoisomers may be separated at any convenient point in the overall synthesis by conventional methods e.g. chromatography. Specific enantiomers may be obtained by resolution of a racemic mixture at any convenient point in the overall synthesis by the use of conventional methods, see for example "Stereochemistry of Carbon Compounds by E. L. Eliel" (McGraw Hill, 1962).

Where it is desired to isolate a compound of the invention as a salt, this may be formed by conventional methods, for example by treatment with an acid or base in a suitable solvent such as an ether (for example diethyl ether), a nitrile (for example acetonitrile), a ketone (for example acetone) a halogenated hydrocarbon (for example dichloromethane) or an ester (for example ethyl acetate). Salts may also be formed by conversion of one salt into another using conventional methods.

Solvates of compounds of formula (I) may conveniently be prepared by crystallisation or recrystallisation from an appropriate solvent.

The invention is further illustrated by the following examples.

All temperatures are in °C. Chromatography was carried out in the conventional manner using silica gel (Merck, 7729) or by flash column chromatography on silica (Merck 9385) and thin layer chromatography (t.l.c) on silica except where otherwise stated. Dried refers to drying with $Na_2SO_4$ unless otherwise indicated.

EXAMPLE 1

8-[(3,4-Dichlorophenyl)acetyl]-7-(1-pyrrolidinylmethyl)-1,4-dioxa-8-aza[4.5]spirodecane hydrochloride

(i) 2-Methyl 1-(phenylmethyl) 3,4-dihydro-4-oxo-1,2(2H)-pyridinedicarboxylate A solution of methyl glyoxylate (1.92 g) and (phenylmethyl) (triphenylphosphoranylidene)carbamate (6.00 g) in benzene (100 ml), was stirred at reflux under nitrogen, for 1 h. A solution of 1-methoxy-3-trimethylsilyloxybutadiene (5.00 g) in benzene (40 ml) was added and the resulting solution stirred at reflux, under nitrogen, for 18 h. The benzene was evaporated in vacuo, and the residue dissolved in tetrahydrofuran (100 ml), treated with 1M hydrochloric acid (10 ml) and stirred at 22° for 1 h. The solution was diluted with ethyl acetate (100 ml), water (40 ml) and the aqueous phase separated. The organic phase was washed with saturated aqueous sodium chloride, dried and evaporated. The residue was purified by chromatography eluting with ethyl acetate-hexane (1:1) to give the title compound as an oil (2.97 g).

Assay Found: C, 61.85; H, 5.25; N, 4.9; $C_{15}H_{15}NO_5$ requires C, 62.3; H, 5.25; N, 4.85%.

(ii) 2-Methyl 1-(phenylmethyl) 4-oxo-1,2-piperidinedicarboxylate

A mixture of the product of stage (i) (2.98 g), tris(triphenylphosphine)rhodium(I)chloride (48 mg), and dimethylphenylsilane (1.7 ml) was stirred in a reacti-vial under nitrogen at 50° C. for 3 h and evaporated in vacuo to give an oil (4.2 g). This oil was dissolved in acetonitrile (65 ml) and 40% aqueous hydrogen fluoride (1 ml, 20 mmol) was added to the solution in a polypropylene vessel. The mixture was allowed to stand at room temperature for 18 h and the solution poured into saturated aqueous sodium bicarbonate (80 ml). After stirring for 2 h, ether (50 ml) was added and the layers separated. The aqueous layer was re-extracted with ether (2×50 ml) and the combined organic solutions were washed with saturated aqueous sodium chloride, dried and evaporated to give an oil (4.2 g). This oil was purified by column chromatography on silica gel eluting with ether-hexane (9:1) to give the title compound as an oil (1.62 g). T.l.c. Silica/Ether-Hexane (9:1) Rf 0.26.

(iii) 7-Methyl 8-(phenylmethyl) 1,4-dioxa-8-azaspiro[4.5]decane-7,8-dicarboxylate A solution of the product of stage (ii) (5.06 g) and 1,2-ethanediol (1.06 ml) in benzene (100 ml) containing 4-toluenesulphonic acid (0.2 g) was stirred at reflux temperature under a Soxhlet cup filled with 4 Å molecular sieves for 4 h. The reaction mixture was allowed to cool to 22°, washed with 2N sodium carbonate (2×20 ml), water (20 ml) and dried. The benzene solution was evaporated in vacuo to give the title compound as an oil (5.75 g).

Assay Found: C,60.55; H,6.35; N,4.4. $C_{17}H_{21}NO_6$ requires C,60.9; H,6.3; N,4.2%.

(iv) Methyl 1,4-dioxa-8-azaspiro[4.5]decane-7-carboxylate

A solution of the product of stage (iii) (5.50 g) in ethyl acetate (60 ml) was hydrogenated over 10% palladium on carbon (0.50 g) for 4 h. The catalyst was filtered off and the filtrate evaporated in vacuo to give the title compound as an oil (3.0 g).

Assay Found: C,53.35; H,7.7; N,6.95. $C_9H_{15}NO_4$ requires C,53.7; H,7.5; N,6.95%.

(v) 1-[(1,4-Dioxa-8-azaspiro[4.5]dec-7-yl)carbonyl]pyrrolidine

A mixture of the product of stage (iv) (0.887 g) and pyrrolidine (2.2 ml) was heated at 150° C. in an autoclave for 2 h, allowed to cool to room temperature and evaporated to dryness giving an oil (1.27 g). This was purified by flash chromatography eluting with chloroformmethanol (9:1), to give an oil which crystallised on standing to give the title compound as a solid (841 mg), m.p. 72.5°–74.5°.

(vi) 7-(1-Pyrrolidinylmethyl)-1,4-dioxa-8-azaspiro[4.5]decane

A solution of the product of stage (v) (712 mg) in dry tetrahydrofuran (7.5 ml) was added dropwise to a stirred suspension of lithium aluminium hydride (total of 363 mg) in dry tetrahydrofuran (15 ml) under nitrogen. The mixture was heated under reflux for 19 h, allowed to cool for 1 h and water (5 ml) was cautiously added dropwise. More water (10 ml) and aqueous sodium hydroxide (2N, 5 ml) were then added followed by chloroform (25 ml). The insoluble material was filtered off, washed thoroughly with chloroform and the filtrate layers separated. The aqueous layer was re-extracted with chloroform (2×25 ml) and the combined organic solution dried and evaporated to give crude title compound (750 mg) as an oil. This oil was purified by column chromatography on neutral activity I alumina (Type UG1, 22.5 g) eluting with ether-methanol (19:1) to give the title compound as an oil (287 mg). T.l.c. Alumina/ether-methanol (19:1) Rf 0.30.

(vii) 8-[(3,4-Dichlorophenyl)acetyl]-7-(1-pyrrolidinylmethyl)-1,4-dioxa-8-azaspiro[4.5]decane hydrochloride A solution of 1,1'-carbonyldiimidazole (200 mg) in warm dry acetonitrile (2.2 ml) was added to a solution of 3,4-dichlorophenylacetic acid (240 mg) in dry acetonitrile (4.2 ml) under dry nitrogen and the mixture stirred at room temperature for 1 h. A solution of the product of stage (vi) (250 mg) in dry acetonitrile (2 ml) was added. Stirring was continued for a further 4 h and the reaction mixture was evaporated in vacuo. The residue was partitioned between chloroform (25 ml) and aqueous sodium carbonate (2N, 12 ml) and the chloroform layer was washed with aqueous sodium carbonate (2N, 12 ml) and water (2×12 ml), dried, and evaporated to dryness giving an oil (580 mg). Purification by flash chromatography eluting with dichloromethane-methanol (9:1) gave the free base of the title compound (347 mg) as an oil. A portion of the free base (289 mg) was dissolved in a mixture of ether (10 ml)-methanol (4 ml) and ethereal hydrogen chloride was added to give the title compound as a solid (250 mg), m.p. 139°–141°.

Analysis Found: C,52.15;H,6.20;N,5.95. $C_{20}H_{26}Cl_2N_2O_3.HCl.0.75H_2O$ requires C,51.85;H,6.20;N,6.05%.

EXAMPLE 2

8-[(3,4-Dichlorophenyl)acetyl]-7-[(1,2,3,6-tetrahydropyridin-1-yl)methyl]-1,4-dioxa-8-azaspiro[4.5]decane hydrochloride (i)
1-[(1,4-Dioxa-8-azaspiro[4.5]dec-7-yl)carbonyl]-1,2,3,6-tetrahydropyridine A mixture of the product of Example 1 stage (iv) (1 g) and 1,2,3,6-tetrahydropyridine (2.8 ml) was heated at 150° C. in a reactivial for 2 h. After cooling the mixture was evaporated in vacuo and the solid residue (800 mg) was purified by flash chromatography eluting with dichloromethane/methanol/ammonia (200:10:1) to give the title compound as an oil (260 mg). T.l.c. Silica. dichloromethane/methanol/ammonia (150:8:1) Rf 0.25.

(ii)
7-[1-(1,2,3,6-tetrahydropyridinyl)methyl]-1,4-dioxa-8-azaspiro[4.5]decane

A solution of the product of Stage (i) (230 mg) in dry tetrahydrofuran (2.5 ml) was added dropwise (5 min) to a stirred suspension of lithium aluminium hydride (115 mg) in dry tetrahydrofuran (6 ml) under dry nitrogen. Stirring under nitrogen at room temperature was continued for 30 min and the mixture was then heated under reflux for 17 h and allowed to cool to room temperature. Water (2 ml) was cautiously added dropwise to the cold mixture under nitrogen to quench the excess reagent. More water (4 ml) and aqueous sodium hydroxide (2N, 2 ml) were added followed by chloroform (10 ml). The mixture was filtered and the filtrate layers separated. The aqueous layer was further extracted with chloroform (20 ml) and the chloroform solutions were combined. dried and evaporated to give the title compound as an oil (230 mg). T.l.c. Alumina/ether-methanol (19:1) Rf 0.36.

(iii)
8-[(3,4-Dichlorophenyl)acetyl]-7-[(1,2,3,6-tetrahydropyridin-1-yl)methyl]-1,4-dioxa-8-azaspiro[4.5]decane hydrochloride A solution of 1,1' carbonyldiimidazole (162 mg) in warm dry acetonitrile (1.8 ml) was added to a solution of 3,4-dichlorophenyl acetic acid in dry acetonitrile (3.4 ml) under nitrogen. After stirring at room temperature for 1 h a solution of the product of stage (ii) (214 mg) in dry acetonitrile (1.6 ml) was added to the mixture. The resulting mixture was stirred under nitrogen and at room temperature for 4 h and allowed to stand for 24 h. The solvent was removed in vacuo and the residue partitioned between chloroform (20 ml) and aqueous sodium carbonate (1M, 10 ml). The chloroform solution was washed with aqueous sodium carbonate (1M, 10 ml) and water (2×10 ml), dried and evaporated to give an oil (430 mg) which was purified by chromatography eluting initially with dichloromethane-ethanol (39:1) and then dichloromethane-methanol (19:1), to give the free base of the title compound (237 mg) as an oil. The oil was dissolved in a mixture of ether (5 ml)-ethyl acetate (5 ml) and ethereal hydrogen chloride was added to give the title compound as a solid (173 mg) m.p. 185°-187°.

Analysis Found: C,54.45; H,5.85; N,5.80.
$C_{21}H_{26}Cl_2N_2O_3 \cdot HCl$ requires C,54.60; H,5.90; N,6.05%.

EXAMPLE 3 cis-Methyl 1-[(3,4-dichlorophenyl)acetyl]-2-(1-pyrrolidinylmethyl)-4-piperidinecarboxylate maleate (1:1)

Methyl 2-methyl-4-pyridinecarboxylate

A solution of potassium permanganate (52.2 g) and 2,4-lutidine (16.5 g) in water (3.41) was heated at 55°-65° for 18 h and then at 60°-65° for 10 h. The reaction mixture was filtered and the colourless filtrate was evaporated in vacuo. Concentrated hydrochloric acid (50 ml) was added and the solvent was removed in vacuo. The solid was suspended in a mixture of toluene (50 ml) and methanol (50 ml) and reevaporated to a paste. The residue was treated with methanol (150 ml) and concentrated sulphuric acid (15 ml), heated at reflux for 6 h and the solvent was removed in vacuo. The residue was cautiously added to aqueous sodium carbonate (2M; 400 ml) and the product was extracted with diethylether (2×200 ml). The ethereal extract was dried ($MgSO_4$) and evaporated leaving an oily residue (14 g) which was purified by distillation to give the title compound as a colourless oil (3.7 g) bp 112°-3° 20 mmHg.

(ii) Methyl 2-(hydroxymethyl)-4-pyridinecarboxylate

A solution of the product of stage (i) in dry chloroform (20 ml) at 0°-5° was treated with a solution of 80%-m-chloroperoxy benzoic acid (8.3 g) in dry chloroform (100 ml), over a 20 min period. The mixture was stirred at ambient temperature for 18 h, and then poured into water (50 ml). The organic solution was washed with 0.5M aqueous sodium bisulphite (50 ml), aqueous sodium carbonate (2M; 100 ml), dried and evaporated to give a solid residue (7 g) which was dissolved in acetic anhydride (15 ml) and heated at 100° for 4 h. The solvent was removed in vacuo leaving an oil which was dissolved in methanol (50 ml) and treated with concentrated sulphuric acid (5 ml). The mixture was heated at reflux for 4 h and the solvent was removed in vacuo. The residue was cautiously added to aqueous sodium carbonate solution (2M; 400 ml) and then extracted with dichloromethane (2×150 ml). The organic extract was dried and evaporated leaving a residue (6 g) which was purified by flash chromatography eluting with dichloromethane/methanol/ammonia 200:8:1 to give the crude product (2.3 g). This was further purified by distillation (Kughelrohr b.p. 100°/10 mmHg) to give the title compound as a solid (1.85 g) m.p. 68°-9°

(iii) Methyl 2-(chloromethyl)-4-pyridinecarboxylate

A solution of the product of stage (ii) in methylacetate (5 ml) was treated with ethereal hydrogen chloride (5 ml). The resulting solid was collected by filtration and added to thionyl chloride (7.5 ml) at 0°-5°. The mixture was stirred at 0°-5° for 3 h and then at ambient temperature for 1 h. Diethyl ether (100 ml) was added and the resulting solid was collected by filtration and washed with diethylether (2×50 ml), to give the title compound as a solid (1.7 g) T.l.c. Silica dichloromethane/methanol/ammonia 75:10:2 Rf 0.8.

(iv) Methyl 2-(1-pyrrolidinylmethyl)-4-pyridinecarboxylate

A solution of product of stage (iii) (1.6 g) in dry dichloromethane (50 ml) at −50° was treated with triethylamine (1.07 ml) and the mixture was stirred for 5 min. A pre-cooled solution of pyrrolidine (1.28 ml) in dry dichloromethane (30 ml) was added at −60° and the mixture was stirred at −60° to 0° for 1 h and at ambient temperature for 72 h. The mixture was poured into aqueous sodium carbonate (1M; 50 ml) and the product was extracted with dichloromethane (50 ml). The organic solution was dried and evaporated leaving an oily residue (1.7 g) which was purified by flash chromatography eluting with dichloromethane/methanol/ammonia 200:10:1 to give the title compound as an oil (0.3 g).

Analysis Found: C,65.37; H,7.34; N,12.69. $C_{12}H_{16}N_2O_2$ requires C,65.43; H,7.32; N,12.72%.

(v) Methyl 2-(1-pyrrolidinylmethyl)-4-piperidinecarboxylate

A solution of the product of stage (iv) (50 mg) in ethanol (2 ml) was hydrogenated at 70 psi and 70° over 5% rhodium on carbon (35 mg) for 14 h. The mixture was filtered and the filtrate was evaporated in vacuo. The residue (0.1 g) was purified by flash chromatography eluting with dichloromethane/methanol/ammonia 200:10:2 to give the title compound as an oil (0.018 g). T.l.c. (Silica/dichloromethane/methanol/ammonia 75:10:2) Rf 0.6.

(vi) cis-Methyl 1-[(3,4-dichlorophenyl)acetyl]-2-(1-pyrrolidinylmethyl)-4-piperidinecarboxylate maleate (1:1)

1,1' Carbonyldiimidazole (0.83 g) was added to a solution of 3,4-dichlorophenylacetic acid (0.6 g) in dry dichloromethane (20 ml) and the mixture was stirred at ambient temperature for 1.5 h. A solution of the product of stage (v) in dry dichloromethane (2 ml) was added and stirring was continued at ambient temperature for 20 h. The mixture was washed with aqueous sodium carbonate (2M; 50 ml), dried and evaporated in vacuo. A solution of the residue (1.2 g) in methanol (50 ml) was treated with concentrated sulphuric acid (0.3 ml) and the mixture was heated at reflux for 4 h. The solvent was evaporated and the residue was basified with aqueous sodium carbonate (2M; 20 ml) and extracted with dichloromethane (2 × 50 ml). The organic solution was dried, filtered and evaporated leaving an oily residue which was purified by flash chromatography eluting with dichloromethane/methanol/ammonia 200:8:1 to give the free base of the title compound as an oil (0.632 g). A sample of the free base (0.1 g) was dissolved in ethyl acetate (5 ml) and treated with maleic acid (0.025 g). The resulting solid was crystallized from methyl acetate (5 ml), to give the title compound as a solid (0.076 g) m.p. 106°-8°.

Analysis Found: C,54.37; H,5.73; N,5.13. $C_{20}H_{26}Cl_2N_2O_3.C_4H_4O_4$ requires C,54.45; H,5.71; N,5.29%.

EXAMPLE 4 trans-1-[(3,4-Dichlorophenyl)acetyl]-2-(1-pyrrolidinylmethyl)-3-piperidinol hydrochloride (i) 2-(Pyrrolidinylmethyl)-3-piperidinol A mixture of 2-(pyrrolidinylmethyl)-3-pyridinol (21.0 g) and platinum oxide (1.0 g) in glacial acetic acid (120 ml) was hydrogenated a 70 psi and room temperature for 20 h. Further platinum oxide (1.0 g) was then added and hydrogenation continued at 70 psi for a further 24 h. The reaction mixture was filtered, the combined filtrates were concentrated in vacuo and the residue was dissolved in water (200 ml). This solution was acidified to pH1 with 5M hydrochloric acid before washing with dichloromethane (2 × 70 ml). The aqueous layer was then basified (pH14) with 5M aqueous sodium hydroxide before extracting with dichloromethane (3 × 70 ml). The combined extracts were washed with 2M aqueous sodium hydroxide (50 ml) and water (50 ml), dried and concentrated in vacuo to give an oil. This crude product was distilled at reduced pressure (Kughelrohr oven, 140°, 0.8 mm Hg) to give the title compound as a waxy solid, (6.17 g) m.p. 45°-50°.

(ii) trans-1-[(3,4-Dichlorophenyl)acetyl]-2-(1-pyrrolidinylmethyl)-3-piperidinol hydrochloride A solution of 3,4-dichlorophenylacetic acid (4.45 g) and 1,1'-carbonyldiimidazole (4.16 g) in dry tetrahydrofuran (60 ml) was stirred at room temperature for 20 min before adding a solution of the product of stage (i) (4.0 g, 60:40 mixture of trans:cis isomers) in dry tetrahydrofuran. This solution was stirred for 16 h under nitrogen and concentrated in vacuo. Column chromatography of the residue on UGI alumina (10 cm diameter, 20 cm length) with graded elution from dichloromethane to dichloromethane:methanol (9:1) removed polar material. The mixture obtained was converted to the hydrochloride salt and crystallised from ethyl acetate:methanol (1:2). The mother liquors were concentrated and the residue was crystallised from the same solvent. The mother liquors from this second recrystallisation gave the title compound upon concentration as an amorphous solid (2.8 g), m.p. 115°-120°, which contained a 93:7 mixture of trans:cis isomers by h.p.l.c.

Analysis Found: C,51.71;H,6.35;N,6.62. $C_{18}H_{24}Cl_2N_2O_2.HCl.0.57H_2O$ requires C,51.71;H,6.02;N,6.70%.

EXAMPLE 5 cis-1-[(3,4-Dichlorophenyl)acetyl]-2-(1-pyrrolidinylmethyl)-3-piperidinol hydrochloride The crystalline material obtained in Example 4 was converted to the free base (1.7 g). Column chromatography of this mixture on UGI alumina (6" length, 2.5" diameter) eluting with dichloromethane: methanol (40:1) gave a poor separation of the two components but allowed the separation of a small amount of the higher running isomer (260 mg). This fraction was converted to the title compound as an amorphous solid (280 mg), m.p. 255°-260° (decomp) which contained a 98:2 mixture of cis:trans isomers by h.p.l.c.

Analysis Found: C,53.0;H,6.28;N,7.26. $C_{18}H_{24}Cl_2N_2O_2.HCl$ requires C,53.0;H,6.18;N,6.87%.

EXAMPLE 6

1-[(3,4-Dichlorophenyl)acetyl]-3-methyl-2-(1-pyrrolidinylmethyl)piperidine maleate (1:1)

(i) cis-1-[(3,4-Dichlorophenyl)acetyl]-3-methyl-2-piperidinemethanol

A solution of 3,4-dichlorophenylacetic acid (1.82 g) and 1,1'-carbonyldiimidazole (1.70 g) in dry tetrahydrofuran (30 ml) was stirred at room temperature under nitrogen for 20 min. A solution of cis-3-methyl-2-piperidinemethanol (1.15 g) in dry tetrahydrofuran (10 ml) was then added and stirring was continued for 16 h. before concentrating the reaction mixture in vacuo. The residue was dissolved in dichloromethane (50 ml), and this solution was washed with 2M hydrochloric acid (50 ml) and saturated aqueous sodium hydrogen carbonate (20 ml), dried and concentrated in vacuo to give a solid. This crude product was crystallised from ethyl acetate:-methanol to give the isomerically pure title compound as needles (1.69 g) m.p. 161°-162°.

(ii)
cis-1-[(3,4-Dichlorophenyl)acetyl]-3-methyl-2-piperidine carboxaldehyde

Dry chromium trioxide (2.88 g) was added portionwise to a stirred solution of dry distilled pyridine (4.6 ml) in dry dichloromethane (40 ml) at room temperature under nitrogen. Stirring was continued for 30 min before adding a solution of the product of stage (i) in dichloromethane (40 ml). After stirring for a further 1 h, the reaction mixture was poured into dry ether (1000 ml). The resulting mixture was filtered and the filtrate concentrated to give a solid. This crude product was purified by flash chromatography eluting with a mixture of ethyl acetate:hexane (1:1) to give the title compound as a solid (1.27 g), m.p. 97°-98°.

(iii)
1-[(3,4-Dichlorophenyl)acetyl]-3-methyl-2-(1-pyrrolidinylmethyl)piperidine maleate (1:1)

A solution of the product of stage (ii) (1.05 g) in dry methanol (5 ml) was added to a stirred mixture of pyrrolidine (1.43 g, 1.68 ml), 5M methanolic hydrogen chloride (3 ml) and activated molecular sieves (3 Å) at room temperature under nitrogen. The resulting mixture was stirred for 15 min before the portionwise addition of sodium cyanoborohydride (230 mg). Stirring was continued for 5 days and the reaction mixture was filtered and the residue washed with methanol. The combined filtrates were concentrated in vacuo and the residue was dissolved in dichloromethane (50 ml). This solution was washed with saturated aqueous sodium carbonate (50 ml) and water (50 ml), dried and concentrated in vacuo to give an oil. The crude product was purified by column chromatography on UGI alumina (6"×2") eluting with ethyl acetate:hexane (1:1) to give the title compound which was isolated as the maleate salt (350 mg) m.p. 190°-191°.

Analysis Found: C,57.22; H,6.59; N,5.72. $C_{19}H_{26}Cl_2N_2O \cdot C_4H_4O_4$ requires C,56.91; H,6.23; N,5.77%.

EXAMPLE 7 trans-1-[(3,4-Dichlorophenyl)acetyl]-2-[(dimethylamino)methyl]-3-piperidinol hydrochloride (i) trans-2-[(Dimethylamino)methyl]-3-piperidinol A mixture of 2-[(dimethylamino)methyl]-3-pyridinol (10.0 g) and platinum oxide (0.5 g) in glacial acetic acid (75 ml) was hydrogenated at 70 psi and room temperature for 72 h. The reaction mixture was filtered and the residue washed with acetic acid (200 ml). The combined filtrates were concentrated in vacuo and the residue was dissolved in 2M hydrochloric acid. This solution was washed with dichloromethane (2×50 ml) before basifying with 5M aqueous sodium hydroxide and extracting with dichloromethane (4×70 ml). The combined extracts were dried and concentrated in vacuo to give an oil (1.8 g). This oil was combined with the crude product from a previous experiment (1.5 g) and distilled at reduced pressure (Kughelrohr, 155°, 2-mbar) to give the title compound, as a waxy solid, (3.2 g) m.p. 50°-60°.

(ii)
trans-1-[(3,4-Dichlorophenyl)acetyl]-2-[(dimethylamino)methyl]-3-piperidinol hydrochloride A solution of 3,4-dichlorophenylacetic acid (2.59 g) and 1,1'-carbonyldiimidazole (2.42 g) in dry tetrahydrofuran (30 ml) was stirred at room temperature under nitrogen for 20 min. A solution of the product of stage (i) (2.0 g) in dry tetrahydrofuran (10 ml) was added and stirring was continued for 16 h before concentrating the reaction mixture in vacuo. The residue was purified by column chromatography on UGI alumina (2.5" diameter×8") with graded elution from dichloromethane/methanol (98:2) to dichloromethane/methanol (9:1) to give the free base of the title compound as an oil (2.7 g). This oil was dissolved in dry diethyl ether (200 ml) and treated with ethereal hydrogen chloride to precipitate the hydrochloride salt which was crystallised from ethyl acetate/methanol to give the title compound as a crystalline solid (0.42 g), m.p. 185°-186°.

Analysis Found: C,50.0; H,5.98; N,7.21. $C_{16}H_{22}Cl_2N_2O_2 \cdot HCl$ requires C,50.3; H,6.07; N,7.34%.

EXAMPLE 8

1-[(3,4-Dichlorophenyl)acetyl]-2-(1-pyrrolidinylmethyl)-4-piperidinone hydrochloride A solution of the product of Example 1 as the free base (2 g) in acetone (120 ml) and dilute sulphuric acid (0.25M, 60 ml) was stirred under reflux for 40 h. The acetone was removed in vacuo and the aqueous residue washed with ether (3×50 ml), basified with aqueous sodium carbonate (1M, 30 ml) and extracted with ethyl acetate (3×50 ml). The combined ethyl acetate extracts were washed with saturated aqueous sodium chloride, dried and evaporated giving an oil (1.76 g), a portion of which (560 mg) was purified by flash chromatography eluting with dichloromethane-methanol (9:1) to give the free base of the title compound as an oil (380 mg). The oil (380 mg) was dissolved in ethyl acetate (5 ml) and ethereal hydrogen chloride was added to give the title compound as a solid (322 mg), m.p. 248°-250°.

Analysis Found: C,53.25; H,5.9; N,6.55. $C_{18}H_{22}Cl_2N_2O_2 \cdot HCl$ requires: C,53.3; H,5.7; N,6.9%.

EXAMPLE 9

1-[(3,4-Dichlorophenyl)acetyl]-4-(3-phenylpropylidene)-2-(1-pyrrolidinylmethyl)piperidine maleate (1:1)

A solution of n-butyl lithium in hexane (1.7 ml, 2.7 mmol) was added dropwise to a stirred, cold (−60° C.) suspension of 3-(phenyl)propyltriphenylphosphonium bromide (1.246 g) in dry tetrahydrofuran (15 ml) under dry nitrogen. After stirring for 1 h the mixture was re-cooled to −60°, a solution of the free base of the compound of Example 8 (500 mg) in dry tetrahydrofuran (2.5 ml) was added and stirring, under nitrogen was continued for 16 h at room temperature. The reaction mixture was quenched with water (10 ml) and the layers separated. The organic layer was evaporated in vacuo and the residue partitioned between water (10 ml) and ether (10 ml). The ether layer was extracted with dilute hydrochloric acid (0.5M, 8 ml) and the acidic extract washed with ether (10 ml), basified with aqueous sodium hydroxide (2M, 3 ml) and the precipitated solid extracted with ether (3×10 ml). The ether extracts were combined, dried and evaporated to give an oil (530 mg) which was purified by column chromatography on UGI alumina eluting with ethyl acetate-hexane (1:1), to give the free base of the title compound as an oil (146 mg). The oil (126 mg) was dissolved in ethyl acetate (2 ml) and added to a solution of maleic acid (35 mg) in ether (4 ml) to give the title compound as a solid, (120 mg) m.p. 134°-135°.

Analysis Found: C,62.30; H,5.95; N,4.60. $C_{27}H_{32}Cl_2N_2O.1.05C_4H_4O_4$ requires C,62.25; H,6.05; N,4.50%.

EXAMPLE 10

N-[1-[(3,4-Dichlorophenyl)acetyl]-2-(1-pyrrolidinylmethyl)-4-piperidinyl]-N-methylacetamide maleate (1:1)

Ethanolic methylamine (33% w/v, 0.84 ml) was added to a stirred suspension of the product of Example 8 (469 mg) in methanol (8 ml) under dry nitrogen. Methanolic hydrogen chloride (5M, 0.23 ml) was added followed by 3 Å molecular sieve (2 g) and sodium cyanoborohydride (110 mg). This mixture was stirred at room temperature for 2 days then more ethanolic methylamine (0.42 ml), methanolic hydrogen chloride (5M, 0.23 ml), and sodium cyanoborohydride (63 mg) were added and stirring was continued for 2 days. The insoluble material was filtered off and the filtrate evaporated to dryness giving an oily solid (480 mg). This solid was partitioned between dilute aqueous sodium hydroxide (pH 12, 5 ml) and dichloromethane (3×5 ml). The dichloromethane extracts were dried (MgSO$_4$) and evaporated to give an oil (387 mg) which was dissolved in pyridine (1 ml). Acetic anhydride (0.55 ml) was added dropwise to the cooled (ice-water bath), stirred solution under nitrogen and the mixture was stirred at room temperature for 18 h. The solvent was removed in vacuo and the residue basified with saturated aqueous sodium bicarbonate (25 ml). The precipitated oil was extracted into dichloromethane (2×25 ml) and the combined extracts dried and evaporated to give an oil (0.54 g) which was purified by column chromatography on UGI alumina eluting with ethyl acetate-ethanol (19:1), to give the impure free base (400 mg). Further purification by chromatography on silica gel eluting with dichloromethane-ethanol-ammonia (125:8:1) gave the free base of the title compound as an oil (233 mg). A solution of the oil in ether (5 ml) was added to a solution of maleic acid (76 mg) in ether (10 ml) to yield an oil. The ether was decanted off and the oil was triturated under ethyl acetate and ether to give the title compound as a solid (238 mg), m.p. 134°-137°.

Analysis Found: C,54.30; H,6.15; N,7.50. $C_{21}H_{29}Cl_2N_3O_2.C_4H_4O_4.0.5\ H_2O$ requires C,54.45; H,6.20; N,7.60%.

EXAMPLE 11 trans-1-[(3,4-Dichlorophenyl)acetyl]-2-(1-pyrrolidinylmethyl)-4-piperidinol maleate (1:1)

A solution of the product of Example 8 as the free base (1.1 g) in ethanol (6 ml) was added dropwise to a stirred suspension of sodium borohydride on alumina (1.7 g of 10% sodium borohydride, ca 4.5 mmol) in ethanol (18 ml). Stirring at room temperature was continued for 1.5 h and dilute hydrochloric acid (1M, 25 ml) was added. The insoluble material was filtered off and washed with water. The filtrate was basified with aqueous sodium carbonate solution (2N, 25 ml) and extracted with dichloromethane. The dichloromethane extracts were dried and evaporated to give a foam (1.09 g) which was purified by column chromatography on neutral UG II alumina (100 g) eluting with dichloromethane-methanol-ammonia (450:8:1), to give the free base of the title compound as a foam (174 mg).

The foam was dissolved in a mixture of ether (10 ml) and dichloromethane (5 ml) and a solution of maleic acid (55 mg) in ether (6 ml) was added. The solvents were removed in vacuo and the residue was triturated under ether (10 ml) and ether (8 ml)/ethyl acetate (2 ml) to give the title compound as a solid (133 mg), m.p. 144°-146°.

Analysis Found: C,53.95; H,5.85; N,5.60. $C_{18}H_{24}Cl_2N_2O_2.C_4H_4O_4$ requires C,54.20; H,5.80; N,5.75%. G.l.c. indicates a trans:cis ratio of 96.4:3.6.

EXAMPLE 12 cis-1-[(3,4-Dichlorophenyl)acetyl]-2-(1-pyrrolidinylmethyl)-4-piperidinol hydrochloride Diisobutyl aluminium hydride (142 ml of a 1M solution in hexane) was added dropwise to a stirred solution of 2,6-di-tert-butyl-4-methylphenol (62.24 g) in dry toluene (590 ml) at 4° under nitrogen. After stirring for 45 min the mixture was cooled to −60° and a solution of the free base of the product of Example 8, (5.2 g) in dry toluene (95 ml) was added over 5 min. The reaction mixture was stirred at −60° for 2 h and allowed to warm to room temperature and stirred at room temperature for a further 1 h. Dilute hydrochloric acid (1M, 500 ml) was added and the resulting mixture was stirred vigorously for 1 h. The layers were separated and the aqueous layer was washed with ether (500 ml), basified with aqueous sodium hydroxide (2M, 500 ml) and extracted with dichloromethane (3×500 ml). The dichloromethane extracts were combined, dried and evaporated to give the free base of the title compound as a foam (4 g) which was shown by g.l.c. to have a cis:trans ratio of 98.6:1.4. A portion of the foam (1 g) was dissolved in a mixture of ether (40 ml)/ethyl acetate (10 ml) and an ethereal solution of hydrogen chloride was added to give a solid (1.07 g). This solid was crystallised from a mixture of ethanol (20 ml)-ethyl acetate (20 ml) to give the title compound (669 mg) as a solid, m.p. 202°-203°.

Analysis Found: C,52.90; H,6.25; N,6.65. $C_{18}H_{24}Cl_2N_2O_2.HCl$ requires C,53.00; H,6.20; N,6.85%.

EXAMPLE 13

1-[(3,4-Dichlorophenyl)acetyl]-2-(pyrrolidinylmethyl)-3-piperidinone hydrochloride Dimethylsulphoxide (0.925 g) in dry dichloromethane (3 ml) was added dropwise to a stirred solution of oxalyl chloride (0.753 g) in dichloromethane (12 ml) at −60° under nitrogen, so as to maintain the internal temperature below −50°. The reaction mixture was stirred for 3 min before adding a solution of the product of Example 4 (2.0 g) in dichloromethane (5 ml) over 5 min. Stirring was continued for 15 min at −60° and triethylamine (2.72 g) was added with stirring. The reaction mixture was allowed to warm to 20° C., water (30 ml) was added, the layers were separated and the aqueous layer was further extracted with dichloromethane (30 ml). The combined organic extracts were dried and concentrated in vacuo to give a solid which was triturated under dry diethyl ether to give the free base of the title compound as an amorphous solid (1.54 g), m.p. 74°-76°. A portion (100 mg) of the free base was dissolved in a minimum amount of diethyl ether/ethyl acetate and treated with ethereal hydrogen chloride to precipitate the title compound as an amorphous solid (85 mg) m.p. 145°–147° (decomp.)

Analysis Found: C,52.88; H,5.75; N,6.85. $C_{18}H_{22}Cl_2N_2O_2.HCl$ requires C,53.28; H,5.71; N,6.9%.

EXAMPLE 14

1-[(3,4-Dichlorophenyl)acetyl]-3-methylene-2-(1-pyrrolidinylmethyl)piperidine maleate (1:1)

A mixture of potassium t-butoxide (129 mg) and methyltriphenylphosphonium bromide (428 mg) in dry tetrahydrofuran (10 ml) was stirred at ambient temperature for 1 h under nitrogen. To the stirred mixture was added a solution of the free base of the compound of Example 13 (369 mg) in dry tetrahydrofuran (5 ml) at 0°. The reaction mixture was allowed to warm to room temperature, stirred for 4 h and quenched with water (10 ml). The mixture was concentrated in vacuo to remove the tetrahydrofuran, acidified with 2N hydrochloric acid (10 ml) and washed with ethyl acetate (2×20 ml). The ethyl acetate washings were re-extracted with 2N hydrochloric acid (10 ml), the two aqueous phases combined, basified with 5N sodium hydroxide solution (20 ml) and extracted with dichloromethane (3×20 ml). The combined extracts were dried, concentrated in vacuo and purified by flash chromatography eluting with dichloromethane:methanol:0.88 ammonia (250:8:1) to give the free base of the title compound as a gum (180 mg). A solution of maleic acid (47 mg) in ethyl acetate was added to a solution of the free base (150 mg) in ethyl acetate. Diethyl ether was added dropwise until the product crystallised to give the title compound as a solid (124 mg) m.p. 124°–125°.

Analysis Found: C,56.78; H,5.75; N,5.68. $C_{19}H_{24}Cl_2N_2O.C_4H_4O_4$ requires C,57.15; H,5.84; N,5.80%.

EXAMPLE 15 trans-1-[(3,4-Dichlorophenyl)acetyl]-2-(1-pyrrolidinylmethyl)-3-piperidinamine dihydrochloride Diethylazodicarboxylate (0.806 g) was added over 5 min. to a stirred solution of triphenylphosphine (1.21 g) in dry tetrahydrofuran (10 ml) at −10° under nitrogen. The resulting mixture was cooled to −70° and diphenylphosphorylazide (1.27 g) was added followed by a solution of 1-[(3,4-dichlorophenyl)acetyl]-2-(pyrrolidinylmethyl)-3-piperidinol (from Example 5) (1.72 g, 82:18 mixture of cis:trans isomers) in dry tetrahydrofuran (5 ml). The resulting mixture was allowed to warm to room temperature over 1 h, stirred for a further 3 h and concentrated in vacuo. The residue was dissolved in diethyl ether (100 ml) and this solution was extracted with 0.2M aqueous hydrochloric acid (50 ml) and 0.1M aqueous hydrochloric acid (30 ml). The combined aqueous extracts were basified to pH 14 before extracting with dichloromethane (3×60 ml). The combined extracts were dried and concentrated in vacuo to give an oil (2.08 g) which contained approximately 25% of the trans-3-azido-[(3,4-dichlorophenyl)acetyl]-2-(1-pyrrolidinylmethyl)piperidine.

The crude azide was dissolved in dry tetrahydrofuran (10 ml) and stirred vigorously with zinc powder (2.0 g) and 1M aqueous potassium dihydrogen orthophosphate (10 ml) at room temperature under nitrogen for 72 h. The reaction mixture was filtered, the filtrate was concentrated in vacuo and the residue was partitioned between 5M hydrochloric acid (30 ml) and diethyl ether (100 ml). The aqueous layer was basified to pH 14 with 5M aqueous sodium hydroxide and extracted with dichloromethane (3×60 ml). The combined extracts were dried and concentrated in vacuo to give an oil which was purified by column chromatography on UG II alumina (6"×1" diameter) with graded elution from dichloromethane:methanol (33:1) to dichloromethane:methanol (10:1) to give the free base of the title compound an oil (350 mg). T.l.c Alumina, Dichloromethane/methanol (20:1) Rf 0.3.

EXAMPLE 16 cis-1-[(3,4-Dichlorophenyl)acetyl]-2-(1-pyrrolidinylmethyl)-4-piperidinecarboxamide hydrochloride A solution of the product of Example 3 as the free base (0.25 g) in a mixture of ethanol (5 ml) and liquid ammonia (50 ml) was heated at 100° for 3 days in an autoclave. The solvent was evaporated and the residue was purified by flash chromatography eluting with dichloromethane/methanol/ammonia 100:10:2 as eluent to give the free base of the title compound as an oil (0.14 g). A solution of the oil in a mixture of diethyl ether and methyl acetate was treated with ethereal hydrogen chloride. The resulting solid was washed with diethyl ether and dried to give the title compound as a solid (0.065 g) T.l.c. Silica, Dichloromethane/ethanol/ammonia (75:10:2) Rf 0.45.

Analysis Found: C,49.79; H,6.12; N,8.82. $C_{19}H_{25}Cl_2N_3O_2.HCl.1.5H_2O$ requires C,49.41; H,6.11; N,9.10.

EXAMPLE 17 cis-1-[(3,4-Dichlorophenyl)acetyl]-2-methyl-6-(1-pyrrolidinylmethyl)piperidine fumarate (1:1)

(i) 2-Methyl-6-(1-pyrrolidinylmethyl)pyridine

A mixture of 6-methylpyridine-2-carboxaldehyde (1.2 g), pyrrolidine (0.78 g) and platinum oxide (0.15 g) in ethanol (50 ml) was hydrogenated at atmospheric pressure for 30 min. The catalyst was filtered off and the filtrate was evaporated. The residue (1.6 g) was purified by chromatography on alumina (60 g, Type UGI), eluting with ether-hexane (1:1) to give the title compound as a colourless mobile oil (1.15 g).

Analysis Found: C, 74.8; H, 9.1; N, 16.2. $C_{11}H_{16}N_2$ requires C, 75.0; H, 9.1; N, 15.9%.

(ii) cis-2 Methyl-6-(1-pyrrolidinylmethyl)piperidine

A mixture of the product of stage (i) (1.0 g) and platinum oxide (0.25 g) in acetic acid was hydrogenated at 80 p.s.i. for 18 h. The catalyst was filtered off, and the filtrate was evaporated in vacuo. The residue was dissolved in dichloromethane and washed with 2N sodium hydroxide and water. The organic extracts were dried (MgSO$_4$) and evaporated and the residue (1.0 g) was purified by chromatography on alumina (60 g, UGI) eluting with ether hexane (1:1) to give the title compound (0.65 g) as an oil. T.l.c. Alumina-dichloromethane-ethanol (20:1), Rf 0.8.

(iii) cis-1-[(3,4-Dichlorophenyl)acetyl]-2-methyl-6-(1-pyrrolidinylmethyl)piperidine fumarate (1:1)

To a stirred solution of 3,4-dichlorophenylacetic acid (0.62 g) in acetonitrile (15 ml) at room temperature was added a solution of 1,1'-carbonyldiimidazole (0.52 g) in acetonitrile (10 ml), followed after 15 min, by a solution of the product of stage (ii) (0.58 g) in acetonitrile (15 ml). After stirring for 8 h at room temperature, the solvent was removed in vacuo and the residue was dissolved in dichloromethane before being washed with 2N sodium carbonate and water. The dried (MgSO$_4$) extracts were evaporated and the residue (1.2 g) was purified by chromatography on alumina (80 g. Type UG1), eluting with ether-hexane (1:1) and (2:1) to give the base as an oil (1.0 g). A portion (0.4 g) was converted to the fumarate salt in ethyl acetate to give the title compound as a solid (0.52 g), m.p. 185°–7°.

Analysis Found: C, 56.6; H, 6.5; N, 5.65. $C_{19}H_{26}Cl_2N_2O.C_4H_4O_9$ requires C, 56.9; H, 6.25; N, 5.75%.

EXAMPLE 18 cis-1-[(3,4-Dichlorophenyl)acetyl]-4-phenyl-2-(1-pyrrolidinylmethyl)piperidine (i) 2-(Chloromethyl)-4-phenylpyridine hydrochloride A solution of 4-phenyl-2-pyridinemethanol (1.57 g) in ether (5 ml) was treated with ethereal hydrogen chloride (ca 5 ml). The resulting solid was filtered off and added to redistilled thionylchloride (7.5 ml) at ca 0°. The brown solution was stirred at ca 0° for 2 h and at 22° for 0.5 h. Ether (100 ml) was added and the resulting solid was filtered off to give the title compound as a solid (1.81 g). T.l.c. Silica (Dichloromethane, ethanol and ammonia 200:8:1) Rf 0.7.

(ii) 4-Phenyl-2-(1-pyrrolidinylmethyl)pyridine

The product from stage (i) (14.0 g) was added to a solution of pyrrolidine (17.0 ml) in water (80 ml) at 22°. The solution was stirred for 1 h at 22° and then potassium hydroxide (40 g), dichloromethane (200 ml) and water (200 ml) were added. The mixture was stirred for 0.25 h and the phases were separated. The aqueous phase was extracted with dichloromethane (100 ml) and the combined organic extracts were washed with water (2×100 ml), saturated brine, dried and evaporated to leave an oil (15.2 g), a portion of which (0.5 g) was purified by flash chromatography eluting with dichloromethane, ethanol and ammonia (200:8:1) to give the title compound as an oil (0.4 g). T.l.c. Silica (Dichloromethane, ethanol and ammonia 200:8:1) Rf 0.4.

(iii) cis-4-Phenyl-2-(1-pyrrolidinylmethyl)piperidine (1)

An excess of ethereal hydrogen chloride was added to a stirred solution of the product of stage (ii) (5.0 g) in ethyl acetate (30 ml). The resulting precipitate was filtered off and crystallised from a mixture of methanol and ethyl acetate to give the hydrochloride salt as a solid (4.3 g). A solution of the salt in glacial acetic acid (100 ml) was hydrogenated at 22° and atmospheric pressure over Adams catalyst (500 mg). When uptake had ceased a further quantity (500 mg) of Adams catalyst was added and the mixture was further hydrogenated. After 20 h the mixture was filtered and the combined filtrate was evaporated to leave an oil. The residue was partitioned between 2N sodium carbonate (100 ml) and dichloromethane (100 ml). The organic phase was dried and evaporated to leave an oil (3.3 g) which was purified by flash chromatography and preparative HPLC to give the title compound as an oil (0.36 g). T.l.c. Silica (dichloromethane/methanol/ammonia 200:8:1) Rf 0.4.

(iv) cis-1-[(3,4-Dichlorophenyl)acetyl]-4-phenyl-2-(1-pyrrolidinylmethyl)piperidine Following the method of Example 1 (vii) the product of stage (iii) (143 mg) gave the title compound as an oil (164 mg) after purification by flash chromatography eluting with dichloromethane/ethanol/ammonia (300:8:1). T.l.c. Silica (dichloromethane, ethanol and ammonia 300:8:1) Rf 0.2.

EXAMPLE 19

Methyl [1-[(3,4-Dichlorophenyl)acetyl]-2-(1-pyrrolidinylmethyl)-4-piperidinylidene]acetate hydrochloride A solution of trimethylphosphonacetate (0.54 g) in dry, distilled tetrahydrofuran (10 ml) was added dropwise to a stirred suspension of sodium hydride (57%, 134 mg, 3.2 mmol) in dry, distilled tetrahydrofuran (40 ml) at 22° under nitrogen. The resulting mixture was stirred for 15 min and treated with a solution of the product of Example 8 in dry, distilled tetrahydrofuran (10 ml). The mixture was heated under reflux for 2.25 h under nitrogen, cooled, diluted with ethyl acetate (50 ml) and washed with saturated brine (50 ml). The aqueous phase was extracted with ethyl acetate (50 ml) and the combined organic extracts were dried and evaporated to leave an oil which was purified by flash chromatography on silica eluting with a mixture of dichloromethane, ethanol and ammonia (300:8:1) to give an oil (0.85 g). The oil was combined with material from a similar reaction (0.7 g) and purified by preparative h.p.l.c. and flash chromatography on triethylamine-deactivated silica eluting with a mixture of hexane, chloroform and triethylamine (60:40:1) to give an oil (130 mg). The oil was dissolved in ether (2 ml) and treated with ethereal hydrogen chloride. The resulting solid was filtered off and washed with ether to give the title compound as a powder (89 mg) m.p. 70°–80°. T.l.c. silica (Dichloromethane, ethanol and ammonia 300:8:1) Multiple elution shows the two isomers at Rf 0.49 and Rf 0.52. H.p.l.c. shows the ratio of isomer I to isomer II to be 86:14. A further quantity of the title compound was obtained from the triethylamine deactivated column but having a ratio of isomers, as detected by h.p.l.c., of 60:40.

EXAMPLE 20

8-[(3,4-Dichlorophenyl)acetyl]-7-(1-pyrrolidinylmethyl)-1-thia-4,8-diazaspiro[4.5]decane hydrochloride A solution of the product of Example 8 (0.22 g) in dry acetonitrile (3 ml) was treated with 2-aminoethanethiol hydrochloride (0.1 g) followed by 4 Å molecular sieves (0.2 g). The reaction mixture was stirred for 18 h, filtered and the filtrate was evaporated in vacuo. The residue was purified by flash chromatography eluting with dichloromethane/methanol/ammonia 200:8:1 to give an oily residue (80 mg) which was dissolved in diethyl ether (10 ml) and treated with ethereal hydrogen chloride to give the title compound as a white solid (65 mg) m.p. 165°–170°. T.l.c. silica (dichloromethane/methanol/ammonia 150:8:1) Rf 0.55.

EXAMPLE 21

8-[(3,4-Dichlorophenyl)acetyl]-7-(1-pyrrolidinylmethyl)-1,4-dithia-8-azaspiro[4.5]decane A solution of the product of Example 8 (0.25 g) and ethanedithiol (0.1 ml) in dry dichloromethane (5 ml) at 0°-5° was treated with borontrifluoride etherate (0.020 ml, 0.16 mmol). The mixture was stirred at ambient temperature for 18 h. Aqueous sodium hydroxide (2M; 5 ml) was added and the product was extracted with dichloromethane (2×15 ml). The combined extracts were dried and evaporated to give an oily residue, which was purified by flash chromatography eluting with dichloromethane/methanol/ammonia 200:8:1 to give a solid which was crystallized from a mixture of methylacetate and hexane to give the title compound as a solid (0.155 g) m.p. 119°-20°. T.l.c. $SiO_2$ Dichloromethane/methanol/ammonia 150:10:2 Rf 0.7.

Analysis Found: C, 53.87; H, 5.79; N, 6.11; S, 14.37. $C_{20}H_{26}Cl_2N_2OS_2$ requires C, 53.92; H, 5.88; N, 6.29; S, 14.40%.

EXAMPLE 22 trans-1-[(3,4-Dichlorophenyl)acetyl]-2-methyl-6-(1-pyrrolidinylmethyl)piperidine salt with fumaric acid (1:1)

(i) trans-2-Methyl-6-(1-pyrrolidinylmethyl)piperidine

A solution of 2-methyl-6-(1-pyrrolidinylmethyl)pyridine (4.75 g) in glacial acetic acid (75 ml) was hydrogenated at atmospheric pressure and room temperature over platinum oxide (0.5 g) for 19 h. The catalyst was filtered off and the filtrate concentrated in vacuo. The residue was dissolved in dichloromethane (100 ml) and the solution washed with aqueous sodium hydroxide (2N, 75 ml and 5N, 20 ml). The aqueous washings were combined and washed with dichloromethane (2×100 ml). The combined extracts were dried and concentrated in vacuo to give an oil (4.56 g) which was purified by vacuum distillation to give a colourless oil (3.7 g) b.p. 120° C./0.4 mbar. An aliquot (2.5 g) was further purified by flash chromatography eluting with dichloromethane-methanol-ammonia (75:8:1) to give initially the cis compound (1.98 g) and subsequently the title compound as a colourless oil (65 mg). T.l.c. Silica/-Dichloromethane;methanol;ammonia (75:8:1) Rf 0.10.

(ii) trans-1-[(3,4-Dichlorophenyl)acetyl]-2-methyl-6-(1-pyrrolidinylmethyl)piperidine salt with fumaric acid (1:1)

The title compound was prepared as a powder (122 mg) from the product of stage (i) (141 mg) by the method of Example 1 (vii) following purification by flash chromatography eluting with dichloromethane/methanol/ammonia (200:8:1) and fumarate salt formation. m.p. 169°-172°.

Analysis Found: C, 56.7; H, 6.25; N, 5.6. $C_{19}H_{26}Cl_2N_2O \cdot C_4H_4O_4$ requires C, 56.9; H, 6.2; N, 5.8%.

EXAMPLE 23 cis-Methyl 1-[(3,4-dichlorophenyl)acetyl]-6-(1-pyrrolidinylmethyl)-3-piperidinecarboxylate hydrochloride (i) Methyl 6-(1-pyrrolidinylmethyl)pyridine-3-carboxylate A solution of methyl 6-methyl-3-pyridinecarboxylate (0.43 g) N-bromosuccinimide (0.59 g) and benzoylperoxide (50 mg) in dry carbon tetrachloride (10 ml) was stirred at 22° and irradiated with a 200 w light bulb for 2 days. Pyrrolidine (2.4 ml) was added and after 15 min the solution was partitioned between dichloromethane (20 ml) and 2N sodium carbonate solution (20 ml). The organic phase was washed with water, saturated brine, dried and evaporated to leave an oil (0.68 g). The oil was purified by flash chromatography eluting with a mixture of dichloromethane, ethanol and ammonia (300:8:1) to give the title compound as an oil (0.22 g). T.l.c. silica (Dichloromethane:methanol: 0.88 ammonia 300:8:1) Rf 0.5.

(ii) cis-Methyl 6-(pyrrolidinylmethyl)-3-piperidinecarboxylate

A solution of the product of stage (i) (4.1 g) in glacial acetic acid (80 ml) was hydrogenated at 22° and atmospheric pressure over Adams' catalyst (3 g). After 3 h the uptake of hydrogen was complete and the mixture was filtered. The filtrate was evaporated to leave an oil which was partitioned between 2N sodium carbonate solution (100 ml) and dichloromethane (100 ml). The aqueous phase was further extracted with dichloromethane (100 ml). The combined organic extracts were washed with saturated brine, dried and evaporated to leave an oil (5.0 g). The oil was purified by flash chromatography eluting with a mixture of dichloromethane, ethanol and ammonia (200:8:1) to give the title compound as an oil (2.6 g). N.m.r.-indicates mixture of cis:-trans (3:1). T.l.c. Silica (Dichloromethane:ethanol: 0.88 ammonia 100:8:1) Rf 0.4.

(iii) (cis)-Methyl 1-[(3,4-dichlorophenyl)acetyl]-6-(1-pyrrolidinylmethyl)-3-piperidinecarboxylate hydrochloride A solution of 3,4-dichlorophenylacetyl chloride (2.53 g) in dry dichloromethane (20 ml) was added dropwise during a period of 15 min to an ice-cold stirred solution of the product of stage (ii) (2.32 g) and dry triethylamine (1.6 ml) in dry dichloromethane (50 ml) and the resulting solution was stirred at 22° for 18 h. The solution was diluted with dichloromethane (20 ml), washed with 2N sodium carbonate solution (50 ml), saturated brine, dried and evaported to leave an oil (4.71 g). The oil was purified by flash chromatography eluting with a mixture of dichloromethane:ethanol: 0.88 ammonia (300:8:1) to give an oil (2.1 g). Repurification by flash chromatography eluting with a mixture of dichloromethane:ethanol: 0.88 ammonia (500:8:1) gave the free base of the title compound as an oil (0.996 g) A portion of the oil (0.15 g) was dissolved in dry ether (5 ml) and an excess of ethereal hydrogen chloride was added. The resulting precipitate was filtered off and crystallised from a mixture of ethyl acetate and hexane to give the title compound as a crystalline solid (98 mg) m.p. 135°-140°.

Assay Found: C, 52.7; H, 6.2; N, 5.9. $C_{20}H_{26}Cl_2N_2O_3 \cdot HCl \cdot 0.42H_2O$ requires C, 52.5; H, 6.1; N, 6.1%.

EXAMPLE 24 trans-Methyl 1-[(3,4-dichlorophenyl)acetyl]-6-(1-pyrrolidinylmethyl)-2-piperidinecarboxylate maleate (1:1)

(i) Methyl 6-(1-pyrrolidinylmethyl)-2-pyridinecarboxylate

The title compound was prepared as an oil (0.28 g) from methyl 6-methyl-2-pyridinecarboxylate (0.43 g) by the method of Example 23 (i) after purification by flash chromatography eluting with dichloromethane/methanol/ammonia (200:8:1). T.l.c. $SiO_2$ Dichloromethane/methanol/ammonia 150:8:1 Rf 0.35.

(ii) trans-Methyl 6-(1-pyrrolidinylmethyl)-2-piperidinecarboxylate

The product of stage (i) (4.8 g) was hydrogenated according to the method of Example 23 (ii) to give the title compound as an oil (0.3 g) after purification by flash chromatography eluting with dichloromethane/ethanol/ammonia (150:8:1). T.l.c. $SiO_2$(Dichloromethane/methanol/ammonia 150:8:1) Rf 0.15.

(iii) trans-Methyl 1-[(3,4-dichlorophenyl)acetyl]-6-(1-pyrrolidinylmethyl)-2-piperidinecarboxylate maleate (1:1)

A mixture of 3,4-dichlorophenylacetic acid (0.325 g) and carbonyldiimidazole (0.26 g) in dry dichloromethane (10 ml) was stirred at ambient temperature for 1 h. A solution of the product of stage (ii) (0.30 g) in dry dichloromethane (10 ml) was added and the mixture was stirred at ambient temperature for 2 days. The reaction mixture was poured into 2M sodium carbonate solution (50 ml) and extracted with dichloromethane (250 ml). The organic extract was washed with 2M sodium carbonate solution (30 ml), dried and evaporated in vacuo. The residue (0.58 g) was purified by flash chromatography eluting with dichloromethane, methanol and ammonia (200:8:1) as eluant to give the free base of the title compound as a gum (0.76 g). The gum was dissolved in ethyl acetate (50 ml) and treated with a solution of maleic acid (60 mg), in ethyl acetate to give a solid which was crystallised from ethyl acetate to give the title compound as a white solid (0.2 g) m.p. 160°–1°.

Assay Found: C, 54.52; N, 5.71; N, 5.17; $C_{20}H_{26}Cl_2N_2O_3 \cdot C_4H_4O_4$ requires C, 54.45; N, 5.71; H, 5.29%.

EXAMPLE 25

1-[(3,4-Dichlorophenyl)acetyl]-6-(1-pyrrolidinylmethyl)-3-piperidinol (i) 5-(Phenylmethoxy)-2-(1-pyrrolidinylmethyl)pyridine A solution of 5-(phenylmethoxy)-2-pyridinemethanol (3.45 g) in methanol (20 ml) was treated with excess ethereal hydrogen chloride. Solvent was evaporated and the residue triturated with ether and filtered. The resulting hydrochloride salt was added over 10 min with ice-cooling to stirred thionyl chloride (14 ml). After 4 h at 0°, ether (200 ml) was added and the precipitate filtered off. It was added over 10 min with ice-cooling and stirring to pyrrolidine (6 ml) and water (12 ml). After stirring for 1 h, the reaction mixture was left to stand for 16 h, diluted with 2N sodium carbonate solution (20 ml) and extracted with dichloromethane (2×20 ml). The extracts were dried and evaporated and the residue purified by flash column chromatography eluting with dichloromethane:ethanol: 0.88 ammonia (200:8:1 to 25:8:1) as eluant to give the title compound as an oil (3.35 g). T.l.c. $SiO_2$ (dichloromethane:ethanol: 0.88 ammonia (100:8:1), Rf 0.32

Analysis Found: C,76.18; H,7.64; N,10.38. $C_{17}H_{20}N_2O$ requires C,76.09; H,7.51; N,10.44%.

(ii) 6-(1-Pyrrolidinylmethyl)-3-piperidinol

A solution of the product of stage (i) (1.06 g) in ethanol (100 ml) was hydrogenated over 5% Rhodium on alumina (1.0 g) at 70 psi and 70° for 18 h. The reaction mixture was filtered and the filtrate was evaporated in vacuo. The residue (0.8 g) was purified by flash column chromatography eluting with dichloromethane/methanol/ammonia 140:10:2 to give the title compound as an oil (0.26 g). T.l.c. Silica(dichloromethane/methanol/ammonia 75:10:2) Rf 0.2.

(iii) 1-[(3,4-Dichlorophenyl)acetyl]-6-(1-pyrrolidinylmethyl)-3-piperidinol

A solution of 3,4-dichlorophenylacetic acid (0.64 g) in dry dichloromethane (15 ml) was treated with 1,1'-carbonyldiimidazole (0.51 g) portionwise over a 5 minute period. The mixture was stirred at ambient temperature for 40 min and was added to a solution of the product of stage (ii) (0.55 g) in dichloromethane (20 ml). The reaction mixture was stirred at ambient temperature for 18 h, diluted with dichloromethane (50 ml) and washed with aqueous sodium carbonate solution (2M; 2×10 ml). The organic extract was dried, filtered, and evaporated in vacuo to give an oily residue (1.1 g). The residue was purified by flash chromatography using dichloromethane methanol/ammonia (200:8:1) as eluent to give the title compound as an oil (0.32 g). T.l.c. Silica(dichloromethane/methanol/ammonia 150:8:1) Rf 0.5.

(iv) 1-[(3,4-Dichlorophenyl)acetyl]-6-(1-pyrrolidinylmethyl)-3-piperidinone hydrochloride The title compound was prepared as a solid (64 mg) from the product of stage (iii) (0.49 g) by the method of Example 13 after purification by flash chromatography eluting with dichloromethane/methanol/ammonia (200:8:1) and hydrochloride salt formation m.p. 193° softens. T.l.c. $SiO_2$(dichloromethane/methanol/ammonia 150:8:1) Rf 0.25.

Assay Found: C,52.72; H,5.87; N,6.80; $C_{18}H_{22}Cl_2N_2O_2 \cdot HCl \cdot 0.4H_2O$ requires C,52.35; H,5.81; N,6.78%.

EXAMPLE 26

7-[(3,4-Dichlorophenyl)acetyl]-8-(1-pyrrolidinylmethyl)-1,4-dioxa-7-azaspiro[4.5]decane hydrochloride A mixture of the product of Example 25 (0.16 g) p-toluenesulphonic acid (0.14 g) and ethanediol (0.1 g) in dry toluene (10 ml) was heated under Dean and Starke conditions for 2 hours. The cooled reaction mixture was diluted with dichloromethane (50 ml) and the organic solution was washed with aqueous sodium carbonate solution (1M; 2×15 ml). The organic solution was dried and evaporated in vacuo. The residue was purified by flash chromatography eluting with dichloromethane/methanol/ammonia (200:8:1) to give the free base of the title compound as a gum (0.12 g). A solution of the free base in dry diethyl ether (10 ml) was treated with ethereal hydrogen chloride. The resulting precipitate was washed with diethyl ether (10 ml) to give the title compound as a solid (0.10 g) m.p. 255° dec. T.l.c. SiO₂(dichloromethane/methanol/ammonia 150:8:1) Rf 0.3.

Assay Found: C,53.31; H,6.02; N,6.12; C₂₀H₂₆Cl₂N₂O₃.HCl requires C,53.40; H,6.05; N,6.23%.

EXAMPLE 27 cis-1-[(4-Chlorophenoxy)acetyl]-2-methyl-6-(1-pyrrolidinylmethyl)piperidine 1,1'-Carbonyldiimidazole (267 mg) was added to a stirred solution of 4-chlorophenoxyacetic acid (310 mg) in dry dichloromethane (20 ml) and the resulting mixture was stirred at room temperature under nitrogen for 1.5 h. A solution of the product from Example 17 (ii) (200 mg) in dry dichloromethane (10 ml) was added and the mixture was stirred for 18 h under nitrogen and heated under reflux for 4 h. The solvent was evaporated and the residue was dissolved in acetonitrile (30 ml) and heated under reflux for 18 h. The solution was washed with sodium carbonate solution (2N, 3×20 ml), dried (MgSO₄) and the organic phase evaporated to give a brown oil (305 mg) which was purified by flash chromatography eluting with dichloromethane:methanol:0.88 ammonia (200:8:1) to give the title compound as a brown oil (124 mg).

Analysis Found: C,64.0; H,7.6; N,7.6. C₁₉H₂₄N₂ClO₂.0.36H₂O requires: C,63.9; H,7.8; N,7.8%. T.l.c. SiO₂ (Dichloromethane:methanol:ammonia: 200:8:1) Rf 0.14.

The following Examples illustrate pharmaceutical formulations containing 8-[(3,4-dichlorophenyl)acetyl]-7-(1-pyrrolidinylmethyl)-1,4-dioxa-8-aza[4.5]spirodecane hydrochloride as active ingredient. Other compounds of formula (I) may be formulated in a similar manner.

| TABLETS FOR ORAL ADMINISTRATION DIRECT COMPRESSION | mg/tablet |
|---|---|
| Active ingredient | 20 |
| Calcium Hydrogen Phosphate B.P.* | 75.5 |
| Croscarmellose sodium USP | 4 |
| Magnesium Stearate. B.P. | 0.5 |
| Compression weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

|  | mg/ml |
|---|---|
| INJECTION FOR INTRAVENOUS ADMINISTRATION |  |
| Active ingredient | 5 |
| Sodium Chloride BP | as required |
| Water for Injection BP 0.5 to 2 ml |  |
| INTRAVENOUS INFUSION |  |
| Dextrose 5% aqueous solution BP | 10-100 ml |
| Active ingredient | 700 mg |
| Sodium Chloride BP | as required |

For infusion at a rate of 700 mg per hour.

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

We claim:

1. A compound of formula (I)

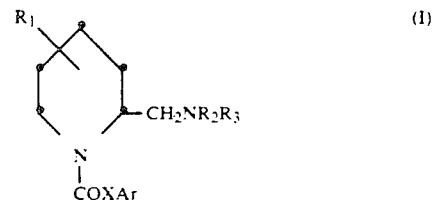

wherein together with the carbon atom to which it is attached,

R₁ forms a 1,3-dithiolane, 1,3-dioxalane, or thiazolidine ring;

R₂ and R₃ are the same or different and represent C₁₋₆alkyl or C₃₋₆alkenyl; or —NR₂R₃ forms a 5-membered ring wherein R₂R₃ together is selected from the group consisting of butylidene, butenylidene, oxypropylidine, and oxypropenylidene or 6-membered ring wherein the ring contains no other heteroatoms in the radical R₂R₃, which ring optionally contains one unit of unsaturation and which is unsubstituted or substituted by hydroxy, oxo, unsubstituted methylidene or methylidene substituted by a group selected from the group consisting of nitrile, phenyl, carboxyl, amido, C₁₋₆alkyl phenyl, (C₁₋₆)alkyl, C₁₋₆hydroxyalkyl, C₁₋₆carboxylalkyl and C₁₋₆amidoalkyl, —COR₆ (where R₆ represents C₁₋₆alkyl, —OR₇ or NHR₇ and R₇ represents hydrogen, C₁₋₆alkyl, phenyl or phen(C₁₋₆)alkyl) or =NOR₈ (where R₈ represents C₁₋₆alkyl);

X represents a direct bond, —CH₂— or —CH₂O—;

Ar represents a phenyl moiety substituted by one or more groups or atoms selected from the group consisting of halogen atoms, C₁₋₆alkyl, CF₃ and NO₂ groups, and physiologically acceptable salts thereof.

2. A compound according to claim 1 wherein the substituent $R_1$ is attached to the 3,4 or 6-position of the piperidine ring.

3. A compound according to claim 1 wherein $—NR_2R_3$ represents a tetrahydropyridine or pyrrolidine ring.

4. A compound according to claim 3 wherein $—NR_2R_3$ represents a pyrrolidine ring.

5. A compound according to claim 3 wherein $R_1$ is at the 4-position.

6. A compound according to claim 5 in which X represents $—CH_2—$ and Ar represents halosubstituted phenyl.

7. A compound selected from
8-[(3,4-Dichlorophenyl)acetyl]-7-[(1,2,3,6-tetrahydropyridin-1-yl)methyl]-1,4-dioxa-8-azaspiro[4.5]-decane;
8-[(3,4-Dichlorophenyl)acetyl]-7-(1-pyrrolidinylmethyl)-1-thia-4,8-diazospiro[4.5]decane;
8-[(3,4-Dichlorophenyl)acetyl]-7-(1-pyrrolidinylmethyl)-1,4-dithia-8-azaspiro[4,5]decane;
and physiologically acceptable salts thereof.

8. 8-[(3,4-Dichlorophenyl)acetyl]-7-(1-pyrrolidinylmethyl)-1,4-dioxa-8-azaspiro[4.5]decane; and its physiologically acceptable salts.

9. A pharmaceutical composition which comprises an effective amount to act as agonists at Kappa receptors of compound of formula (I) as defined in claim 1 or a physiologically acceptable salt thereof together with a pharmaceutically acceptable carrier therefor.

10. A method of treating a human suffering from pain or cerebral ischaemia which comprises administering an analgesically effective amount of a compound of formula (I) as defined in claim 1 or a physiologically acceptable salt.

* * * * *